(12) United States Patent
Chang et al.

(10) Patent No.: US 8,586,095 B2
(45) Date of Patent: Nov. 19, 2013

(54) THERMOSENSITIVE NANOSTRUCTURE FOR HYPERTHERMIA TREATMENT

(75) Inventors: Wen Hsiang Chang, Taipei (TW); Chao-Hung Kao, Taipei (TW); Chin-I Lin, Tainan County (TW); Shian-Jy Wang, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 1880 days.

(21) Appl. No.: 11/511,464

(22) Filed: Aug. 29, 2006

(65) Prior Publication Data

US 2007/0154397 A1 Jul. 5, 2007

(30) Foreign Application Priority Data

Dec. 30, 2005 (TW) .................................. 94147648

(51) Int. Cl.
*A61K 9/16* (2006.01)
(52) U.S. Cl.
USPC ............ 424/490; 424/489; 424/9.3; 424/9.32
(58) Field of Classification Search
USPC ....................................................... 424/490
See application file for complete search history.

(56) References Cited

U.S. PATENT DOCUMENTS

| | | | | |
|---|---|---|---|---|
| 6,039,557 A | * | 3/2000 | Unger et al. | 425/429 |
| 6,149,576 A | | 11/2000 | Gray et al. | |
| 2003/0069619 A1 | | 4/2003 | Fenn et al. | |
| 2005/0059878 A1 | | 3/2005 | Winter | |
| 2007/0148251 A1 | * | 6/2007 | Hossainy et al. | 424/489 |
| 2007/0191377 A1 | * | 8/2007 | Worcel | 514/248 |

FOREIGN PATENT DOCUMENTS

| | | |
|---|---|---|
| TW | 228134 | 8/1994 |
| TW | 476654 | 2/2002 |
| TW | 542733 | 7/2003 |
| TW | M2524733 | 12/2004 |
| WO | WO-03/026618 A1 | 4/2003 |
| WO | WO-2005/044365 A2 | 5/2005 |

* cited by examiner

*Primary Examiner* — James Rogers
(74) *Attorney, Agent, or Firm* — Birch, Stewart, Kolasch & Birch, LLP

(57) ABSTRACT

A thermosensitive nanostructure for hyperthermia treatment. Magnetic nanoparticles are encapsulated in a thermosensitive polymer nanostructure having a lower critical solution temperature (LCST) of about 40-45° C. The thermosensitive polymer nanostructure may carry a drug. When the magnetic nanoparticles are heated to 40-45° C. by application of an alternating magnetic field in hyperthermia treatment, the thermosensitive polymer nanostructure collapses to release the drug, thus providing concurrent drug treatment.

10 Claims, 8 Drawing Sheets

THERMOSENSITIVE NANOSTRUCTURE FOR HYPERTHERMIA TREATMENT

BACKGROUND OF THE INVENTION

1. Field of the Invention

The invention relates to nanobiotechnology, and in particular to a thermosensitive nanostructure for hyperthermia treatment.

2. Description of the Related Art

One of the targeted area of nanobiotechnology is based on nanomaterials and technology in conjunction with molecular biology techniques through the use of various molecular modified nanomaterials or components including dendrimer, nanotube, nanoparticles, or quantum dot for application in medical examination and treatment, drug delivery, transplant, biomimetic sensing, genetic therapy, immunological diagnosis and MRI (Magnetic Resonance Imaging) developer.

Hyperthermia has been proposed as a cancer treatment. It is understood that tumor cells are reliably more sensitive to heat than normal cells. In magnetic hyperthermia treatment, magnetic particles are subjected to an applied alternating magnetic field to generate heat at the tumor site. Superparamagnetic iron oxide nanoparticles are the most frequently used material in magnetic hyperthermia because they can absorb the magnetic field more efficiently and are more easily dispersed than micron-particles. Typically, the iron oxide nanoparticles are surface modified to improve the biocompatibility.

In the field of drug delivery systems, nanomaterials such as thermo-, pH-, photo-sensitive or enzyme degradable polymers are widely investigated as carrier for controlled drug delivery. The drug encapsulated in the carrier is released in a controlled manner as the carrier reaches the target site.

The invention aims to provide nanomaterials for use in magnetic hyperthermia in conjunction with targeted drug delivery.

BRIEF SUMMARY OF THE INVENTION

It is a general object of the invention to provide a thermosensitive nanostructure for hyperthermia treatment, which can release a drug when heated in hyperthermia treatment, thereby providing concurrent drug treatment.

To achieve the above object, the invention provides a thermosensitive nanostructure for hyperthermia treatment, comprising a thermosensitive polymer nanostructure having a lower critical solution temperature (LCST) of about 40-45° C.; and magnetic nanoparticles encapsulated in the thermosensitive polymer nanostructure. In addition, a drug or NO donor may be encapsulated in the nanostructure.

The thermosensitive nanostructure may be grafted with specific targeting ligand to identify specific tumor sites or other lesions. Surprisingly, the thermosensitive polymer nanostructure of the invention may increase the r2 value of the encapsulated magnetic nanoparticles, resulting in greater contrast enhancement on MRI. Furthermore, the encapsulated magnetic nanoparticles may induce heat more efficiently in hyperthermia. The specific absorption rate (SAR) of the magnetic nanoparticles is about 1.5 times that of commercial developer, RESOVIST® from Schering Corporation.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The invention provides a thermosensitive polymer nanostructure having a lower critical solution temperature (LCST) of about 40-45° C., more preferably about 42-45° C. Note that in magnetic hyperthermia treatments, magnetic nanoparticles are typically heated to the same temperature range by application of an alternating magnetic field. As such, the thermosensitive polymer nanostructure will undergo a phase change during the process of hyperthermia treatment and release the drug encapsulated in the nanostructure to provide in-situ concurrent drug treatment.

Figure 1:
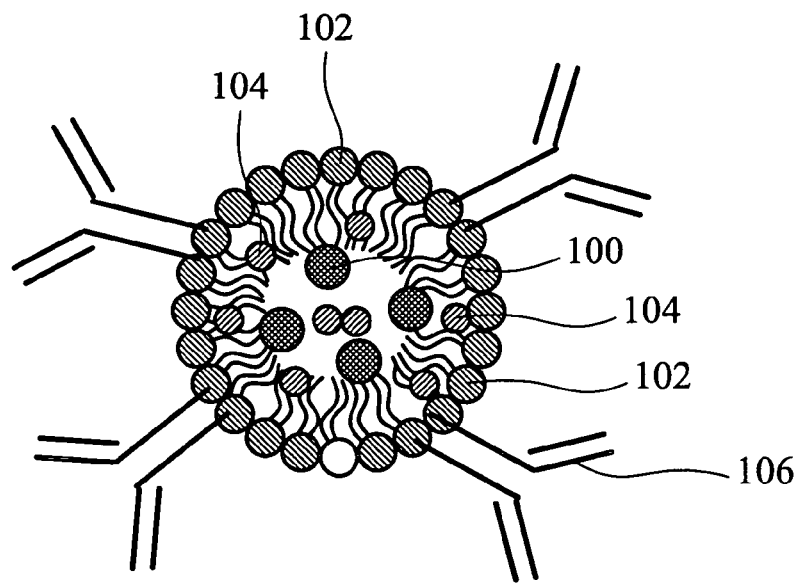
FIG. 1 is a schematic view showing a thermosensitive nanostructure according to one embodiment of the invention.
Figure 2:
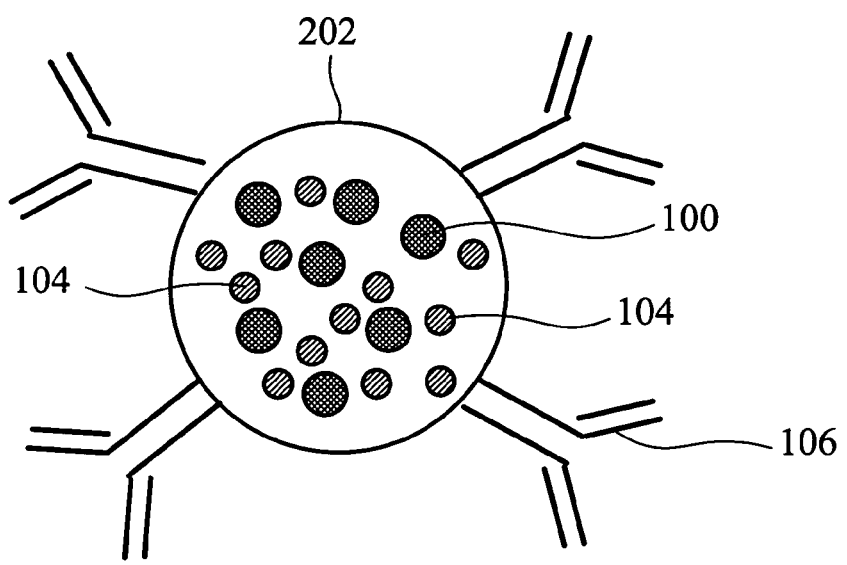
FIG. 2 is a schematic view showing a thermosensitive nanostructure according to another embodiment of the invention.

The thermosensitive polymer nanostructure of the invention may include diblock copolymers, triblock copolymers, or latex. FIGS. 1 and 2 illustrate two basic types of nanostructures according to the invention. FIG. 1 shows that the nanostructure may be a micelle composed of a plurality of copolymers 102 having critical micelle concentration (CMC) behavior. An exemplary copolymer 102 is PEG-PLGA-PEG triblock copolymer (Mw: 750-2810-750). It is to be understood that many copolymer units may be used for the invention as long as their copolymer exhibits a lower critical solution temperature (LCST) of about 40-45° C. As well as polyethylene glycol (PEG) and poly(glycolide co-lactide) (PLGA), other suitable polymer units include polylactic acid (PLA), PLA-PEG, poly(glycolic acid) (PGA), poly(ε-caprolactone) (PCL), poly(methyl methacrylate) (PMMA), and the like.

FIG. 2 shows that the nanostructure of the invention may be in the form of a thermosensitive polymer nanoparticle 202. An exemplary thermosensitive polymer nanoparticle 202 is a copolymer of acrylic acid (AA) and N-isopropylacrylamide (NIPAAm), a thermosensitive monomer. Likewise, it is to be understood that acrylic acid (AA) may be replaced with other copolymer units such as N-vinylpyrrolidone (VPD), and other types of thermosensitive copolymers may be used as long as they exhibit a lower critical solution temperature (LCST) of about 40-45° C. Other suitable thermosensitive copolymers include but are not limited to PDEAAm, PEOz (poly(oxazoline), and PBMA (poly(butylmethacrylate)).

As shown in FIGS. 1 and 2, magnetic nanoparticles 100 and optionally a therapeutic drug or NO donor 104 are encapsulated in the thermosensitive nanostructure of the invention. The magnetic nanoparticles 100 are preferably made of at least one of Fe, Co, Ni, and oxides thereof. It will be appreciated that the nanoparticles can be made of any single or composite magnetic material, although superparamagnetic materials are particularly preferred. The magnetic nanoparticles 10 preferably have a diameter of about 8-100 nm, and the thermosensitive nanostructure preferably has a diameter of about 10-300 nm.

The surfaces of the thermosensitive nanostructure are typically provided with hydrophilic groups such as hydroxyl, amine, or carboxyl groups. Preferably, a targeting ligand 106 is grafted to the surfaces of the nanostructure. Those skilled in the art can attach any suitable targeting ligands on the nanostructure to provide specificity. Commonly used targeting ligands include antibodies, proteins, peptides, enzymes, carbohydrates, glycoproteins, nucleotides, and lipids. For example, folic acid can be used to specify breast cancer cells with folate receptor.

Figure 3:
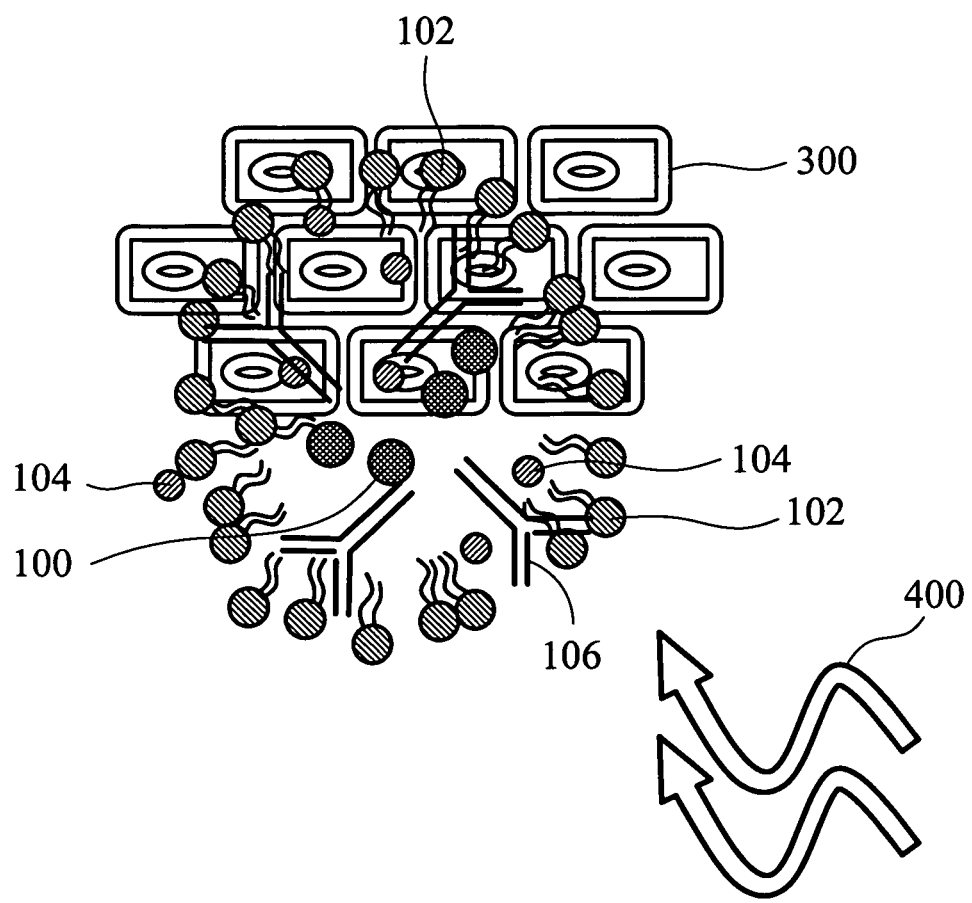
FIG. 3 is a schematic view of collapse of the thermosensitive nanostructure when subjected to an alternating magnetic field in hyperthermia treatment.

FIG. 3 is a schematic view showing the phase change of the thermosensitive nanostructure during hyperthermia treatment. When the nanostructure is administrated to the tumor cell 300 by the help of the targeting ligand 106, the magnetic nanoparticles 100 are subjected to an alternating magnetic field 400 to execute the hyperthermia treatment. As the temperature reaches the LCST (40-45° C.) of the thermosensitive nanostructure, it collapses and releases the carried drug 104 at the tumor site to further facilitate the treatment.

The nanostructure of the invention is also effective in treating brain tumors. In this application, a NO donor can be encapsulated in the nanostructure to increase blood-brain barrier (BBB) permeability. In one embodiment, after the nanostructure is administrated to a patient by intravenous injection, an alternating magnetic field is applied to the patent's brain to heat the magnetic nanoparticles to about 40° C. to allow for the NO donor to diffuse out from the nanostructure. The NO donor releases NO to attenuate blood-brain barrier (BBB) such that the magnetic nanoparticles can cross the blood-brain barrier to reach the brain tumor. Thereafter, the magnetic nanoparticles are heated to a higher temperature, for example, about 42-45° C. to proceed hyperthermia treatment.

Experimental results indicate that the nanostructure of the invention may increase the r2 value of the magnetic nanoparticle 100 to about 1-5 times of commercial developer, RESOVIST® from Schering Corporation. Accordingly, the magnetic nanoparticle may provide greater contrast enhancement when being a MRI contrast agent.

Without intending to limit it in any manner, the invention is further illustrated by the following examples.

Example 1

PEG-PLGA-PEG Preparation 6.35 g of methoxy polyethylene glycol (mPEG; molecular weight=750), 9.68 g of lactide, and 2.2 g of glycolide were placed under high vacuum for 6 hours to remove water. Under nitrogen, 100 µl of SnOct was added to the above mixture for reaction for 24 hours at 160° C. Subsequently, the resulting mixture was cooled to room temperature, followed by addition of 50 ml of tetrahydrofuran (THF) to dissolve the reaction polymer. Polymer solution was slowly added to 500 ml of ethyl ether to re-precipitate the polymer. The precipitant was collected and dried to give a diblock polymer.

The diblock copolymer was added to 250 ml of toluene, and some toluene was distilled out until about 60 ml remained. Next, 0.75 ml of HMDI (hexamethylene dissocyanate) and 100 µl of SnOct were added for reaction. The reaction mixture was stirred at 60° C. for 12 hours, refluxed for 6 hours, and then cooled to room temperature to precipitate the polymer. After removing the toluene, 30 ml of dichloromethane was used to dissolve the polymer, and 500 ml of ethyl ether was then slowly added to re-precipitate the polymer. The precipitate was collected and dissolved in 50 ml of THF, and again, 500 ml of ethyl ether was used to re-precipitate the polymer. Finally, the precipitate was collected and dried to provide the PEG-PLGA-PEG triblock copolymer.

The molecular weight of the obtained copolymer was measured by gel permeation chromatography (GPC), giving number-average molecular weight (Mn) of 4655, weight-average molecular weight (Mw) of 5230, and polydispersity index (PDI) of 1.12. The critical micelle concentration (CMC) of the copolymer was measured as 0.001 mg/ml.

Figure 4:
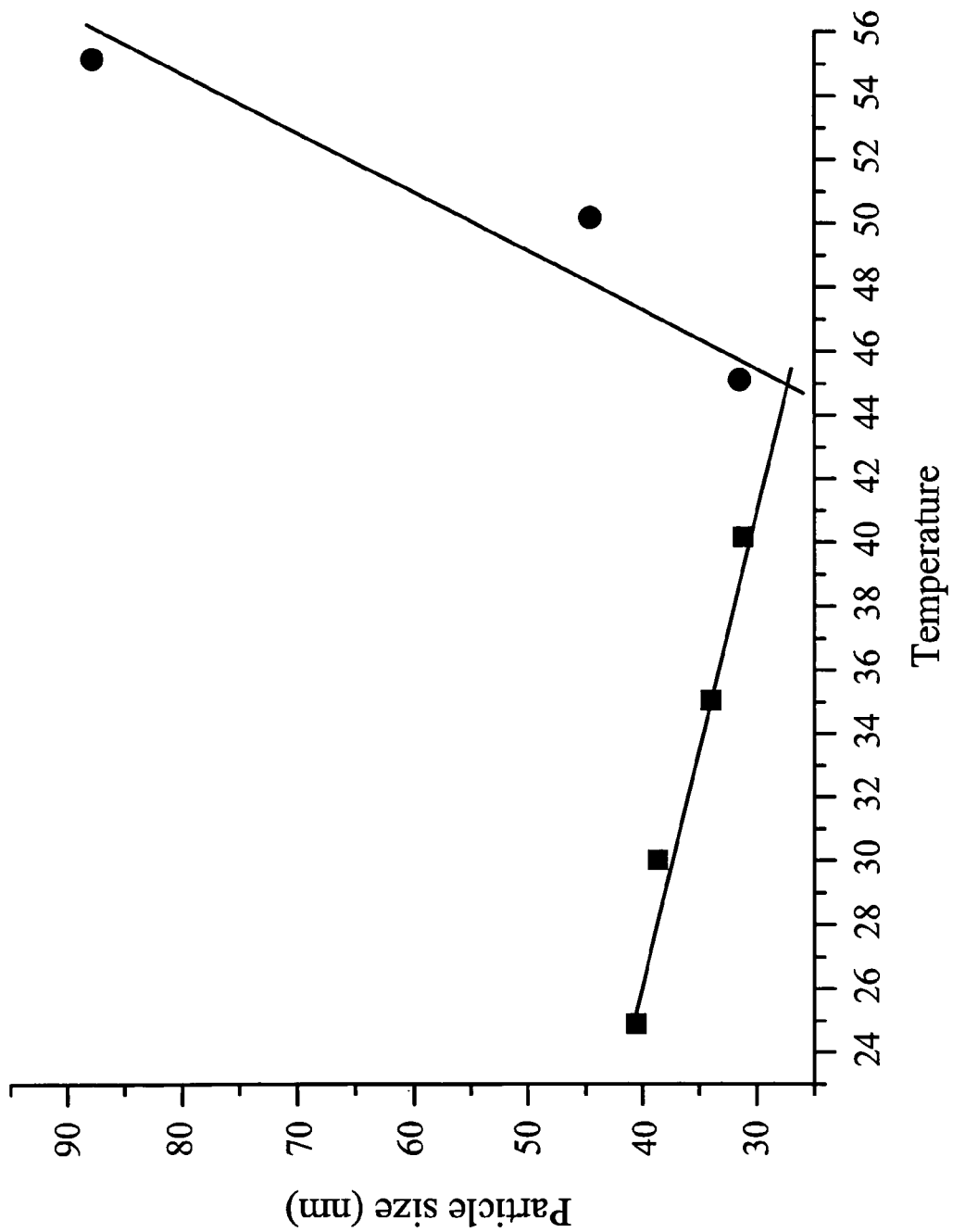
FIG. 4 is a graph showing the relationship between the particle size of PEG-PLGA-PEG of Example 1 and temperature.

The copolymer was further dissolved in THF to provide a solution with a concentration of 40 mg/ml. The THF solution was injected to deionized water with a ratio of 1:4 (THF: deionized water), and sonicated for 10 minutes. Thereafter, the solution was concentrated under vacuum, and filtered with 0.45 µm filter paper. FIG. 4 is a graph showing particle size of PEG-PLGA-PEG varying with temperature. The particle size increases drastically with temperatures over 45° C.

Example 2

Micelle Encapsulation of Iron Oxide

The PEG-PLGA-PEG of Example 1 was dissolved in THF to provide a solution with a concentration of 40 mg/ml. The THF solution was injected to a solution containing iron oxide nanoparticles with a ratio of 1:4, and sonicated for 2 minutes. Thereafter, the solution was concentrated under vacuum, and filtered with 0.45 µm filter paper. Table 1 shows the measured particle size at different temperatures.

TABLE 1

| | Temperature | | | |
|---|---|---|---|---|
| | 25° C. | 30° C. | 37° C. | 45° C. |
| Particle size | 113.6 nm | 75.6 nm | 141.4 nm | 267.4 nm |

Figure 5:
FIG. 5 is a TEM micrograph of PEG-PLGA-PEG of Example 1 with encapsulated iron oxide nanoparticles.

The phase transformation behavior of the micelle was also observed visually. The solution appeared to be a transparent, brown solution at 25° C., but turned into a turbid suspension at 45° C. FIG. 5 shows a TEM (Transmission Electron Microscope) micrograph of PEG-PLGA-PEG with encapsulated iron oxide nanoparticles.

The encapsulated iron oxide nanoparticles were measured for r1 and r2 values with results listed in Table 2. Surprisingly, the r2 value was about twice that of RESOVIST® (from Schering Corporation).

TABLE 2

|  | r1 | r2 |
|---|---|---|
| Iron oxide encapsulated in diblock copolymer of Example 1 | 17.3 mM$^{-1}$S$^{-1}$ | 308.4 mM$^{-1}$S$^{-1}$ |
| Iron oxide encapsulated in triblock copolymer of Example 1 | 19.8 mM$^{-1}$S$^{-1}$ | 344 mM$^{-1}$S$^{-1}$ |
| RESOVIST ® | 23 mM$^{-1}$S$^{-1}$ | 160 mM$^{-1}$S$^{-1}$ |

Specific absorption rate (SAR) of the encapsulated nanoparticles was measured with results shown in Table 3. The specific absorption rate of the encapsulated magnetic nanoparticles is about 1.5 times that of RESOVIST® (from Schering Corporation).

TABLE 3

|  | SAR |
|---|---|
| Iron oxide encapsulated in triblock copolymer | 34.4 Watt/g of Fe |
| Resovist ® | 20.5 Watt/g of Fe |

Example 3

Micelle Encapsulation of Drug

Different amounts of PEG-PLGA-PEG of Example 1 and Paclitaxel were dissolved in THF to provide sample solutions of varying concentrations. Each solution was injected to deionized water and THF and non-capsulated drug were then removed by dialysis. The ingredients and amounts of each sample are given in Table 4.

TABLE 4

| Sample no. | Paclitaxel | PEG-PLGA-PEG | THF | Deionized water |
|---|---|---|---|---|
| No. 1 | 20 mg | 40 mg | 2.5 mL | 10 mL |
| No. 2 | 10 mg | 50 mg | 2.5 mL | 10 mL |
| No. 3 | 10 mg | 100 mg | 2.5 mL | 10 mL |
| No. 4 | 6.7 mg | 100 mg | 2.5 mL | 10 mL |

In Samples 1-3, the copolymer and Paclitaxel were precipitated from deionized water. In Sample 4, the copolymer formed into micelles and encapsulated Paclitaxel. A standard curve of drug concentration versus absorbance was obtained at ultraviolet wavelength 227 nm. The solution after dialysis was left standing at room temperature and 45° C. for 60 minutes. Thereafter, the solution was fed to an ultrafiltration concentration device to collect the filtrate. The percentage of drug release calculated from the standard curve is listed in Table 5.

TABLE 5

| Weight ratio of polymer to drug | 15/1 |
|---|---|
| Loading efficacy | 5.63% |
| Percentage of drug release | 5.28% |

Loading efficacy: [drug weight/(drug weight + copolymer weight)] × 100%
Percentage of drug release: released drug/carried drug before release × 100%

Example 4

Nanoparticle Encapsulation of Iron Oxide

In this example, thermosensitive polyNiPAAm nanoparticle was prepared, cooled to 4° C. to swell the nanoparticle for iron oxide to diffuse into, and then returned to room temperature. The detailed procedure was as follows.

3 g of polyNiPAAm, 89.97 μg of acrylic acid, 0.15 g of NN'-methylene-bis-acrylamide, and 0.15 g of emulsifier PLURONIC F127 were added to 270 ml of deionized water, thoroughly stirred for 15 minutes, and heated to 70° C. with a water bath.

Thereafter, 1.5 mmol of ammonium persulphate (APS) in 30 ml of deionized water was added to the solution for reaction at 70° C. for 3 hours with an agitation rate of 300 rpm.

Figure 6:
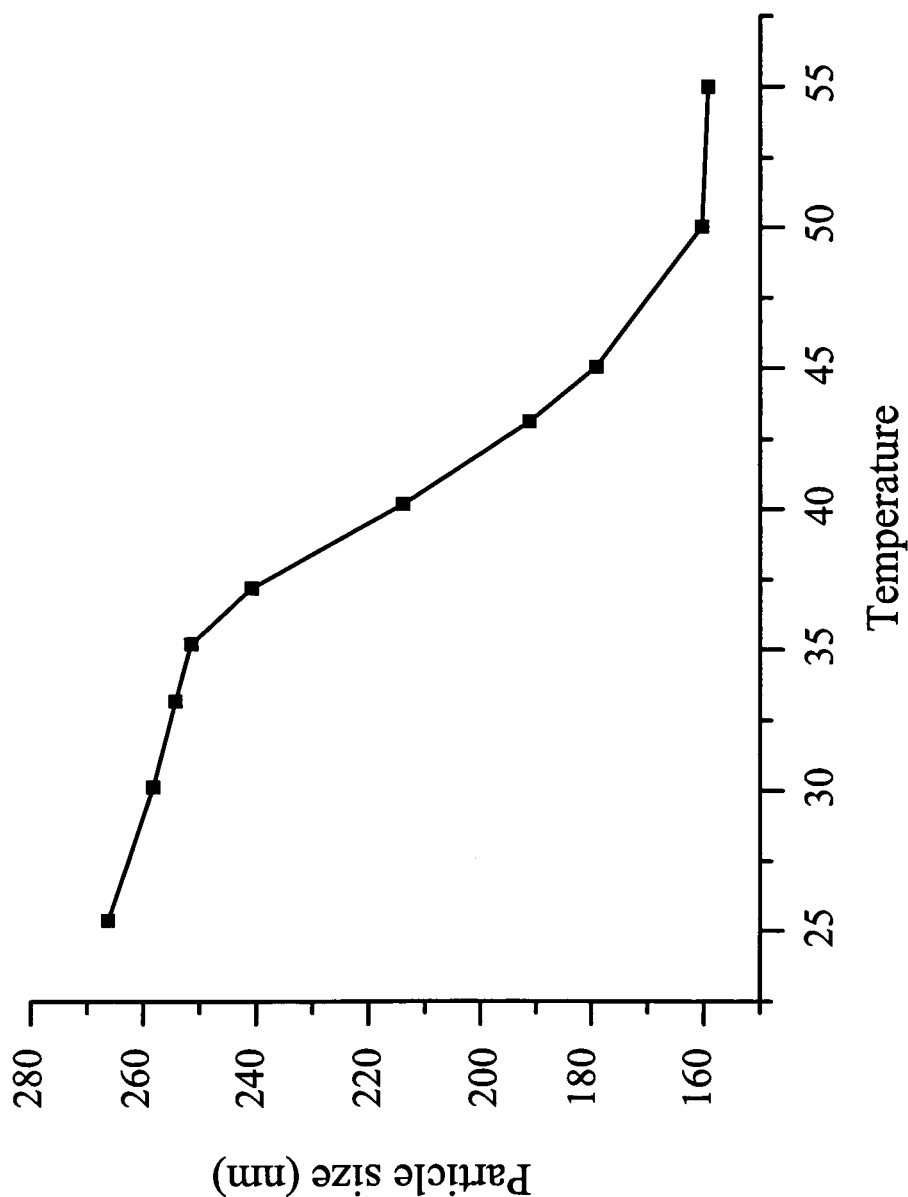
FIG. 6 is a graph showing the relationship between the particle size of polyNiPAAm-co-AA of Example 4 and temperature.
Figure 7:
FIG. 7 is a TEM micrograph of polyNiPAAm-co-AA of Example 4 with encapsulated iron oxide nanoparticles.

After reaction, the solution was cooled to room temperature, and the monomer in the solution was removed in water through a dialysis membrane (MWCO: 12000-14000). The solution was cooled to 4° C., followed by addition of iron oxide nanoparticles and left standing for 12 hours before returned to room temperature. FIG. 6 is a graph showing particle size of polyNiPAAm-co-AA varying with temperature. FIG. 7 is a TEM micrograph of polyNiPAAm-co-AA with encapsulated iron oxide nanoparticles.

Example 5

Nanoparticle In-Situ Encapsulation of Iron Oxide

In this example, iron oxide nanoparticles were encapsulated during the synthesis of thermosensitive polyNiPAAm nanoparticle. The detailed procedure was as follows.

3 g of polyNiPAAm, 89.97 μg of acrylic acid, 0.15 g of NN'-methylene-bis-acrylamide, 0.15 g of emulsifier PLURONIC F127, and 2 ml of iron oxide nanoparticle (1.122 mg/ml) were added to 270 ml of deionized water, thoroughly stirred for 15 minutes, and heated to 70° C. with a water bath.

Thereafter, 0.3423 g of ammonium persulphate in 30 ml of deionized water was added to the solution for reaction at 70° C. for 3 hours with an agitation rate of 500 rpm.

Figure 8:
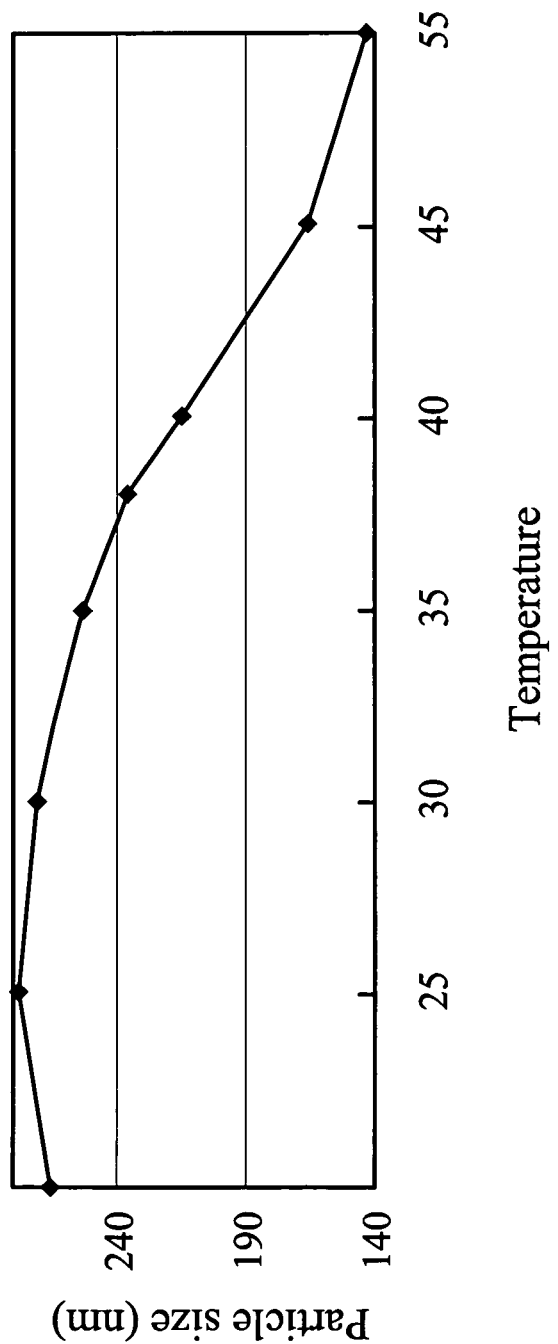
FIG. 8 is a graph showing the relationship between the particle size of polyNiPAAm-co-AA of Example 5 and temperature.
Figure 9:
FIG. 9 is a TEM micrograph of polyNiPAAm-co-AA of Example 5 with encapsulated iron oxide nanoparticles.

After reaction, the solution was cooled to room temperature, and the monomer in the solution was removed in water through a dialysis membrane (MWCO: 12000-14000). The solution was filtered using 0.45 μm filter paper, and the pH value was adjusted to about 7.4. FIG. 8 is a graph showing particle size of polyNiPAAm-co-AA varying with temperature. FIG. 9 is a TEM micrograph of polyNiPAAm-co-AA with encapsulated iron oxide nanoparticles.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A thermosensitive nanostructure for hyperthermia treatment, comprising:
    a thermosensitive polymer nanostructure having a lower critical solution temperature (LCST) of about 42-45° C., wherein the thermosensitive polymer nanostructure comprises a triblock copolymer of PEG-PLGA-PEG having a weight-average molecular weight (Mw) of 5230, or polyNiPAAm-co-AA having a molecular weight cut off (MWCO) of 12000-14000; and
    magnetic nanoparticles encapsulated in the thermosensitive polymer nanostructure,
    wherein PEG is polyethylene glycol, PLGA is poly(glycolide co-lactide), NiPAAm is N-isopropylacrylamide, and AA is acrylic acid.

2. The thermosensitive nanostructure as claimed in claim 1, wherein the thermosensitive polymer nanostructure is a micelle.

3. The thermosensitive nanostructure as claimed in claim 1, wherein the thermosensitive polymer nanostructure has a diameter between about 10 and 300 nm.

4. The thermosensitive nanostructure as claimed in claim 1, wherein the thermosensitive polymer nanostructure is provided with hydroxyl, amine, or carboxyl groups.

5. The thermosensitive nanostructure as claimed in claim 1, wherein the thermosensitive polymer nanostructure is grafted with a ligand.

6. The thermosensitive nanostructure as claimed in claim 1, further comprising a drug encapsulated in the thermosensitive polymer nanostructure, wherein the drug is released during hyperthermia treatment.

7. The thermosensitive nanostructure as claimed in claim 1, further comprising a NO donor encapsulated in the thermosensitive polymer nanostructure, wherein NO is nitrogen monoxide.

8. The thermosensitive nanostructure as claimed in claim 1, wherein the magnetic nanoparticles are contrast agents for magnetic resonance imaging (MRI).

9. The thermosensitive nanostructure as claimed in claim 1, wherein the thermosensitive polymer nanostructure increases r2 value of the magnetic nanoparticles.

10. The thermosensitive nanostructure as claimed in claim 1, wherein the thermosensitive polymer nanostructure increases specific absorption rate (SAR) of the magnetic nanoparticles.

\* \* \* \* \*